United States Patent
Cahan et al.

(10) Patent No.: US 10,973,732 B2
(45) Date of Patent: Apr. 13, 2021

(54) ACTIVE ADAPTABLE COMPRESSION STRUCTURES

(71) Applicant: INTERNATIONAL BUSINESS MACHINES CORPORATION, Armonk, NY (US)

(72) Inventors: Amos Cahan, Dobbs Ferry, NY (US); Theodore G. van Kessel, Millbrook, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 571 days.

(21) Appl. No.: 15/838,393

(22) Filed: Dec. 12, 2017

(65) Prior Publication Data
US 2018/0116857 A1    May 3, 2018

Related U.S. Application Data

(62) Division of application No. 15/337,523, filed on Oct. 28, 2016, now Pat. No. 9,889,038.

(51) Int. Cl.
*A61H 9/00* (2006.01)
*A61F 5/32* (2006.01)
(Continued)

(52) U.S. Cl.
CPC .............. *A61H 9/0085* (2013.01); *A61F 5/32* (2013.01); *A61F 5/34* (2013.01); *A61H 9/00* (2013.01);
(Continued)

(58) Field of Classification Search
CPC ........ A61H 9/00; A61H 9/005; A61H 9/0078; A61H 9/0085; A61H 9/0092; A61H 11/00; A61H 2011/005; A61H 2203/04; A61H 2205/10; A61H 2205/106; A61H 2205/108; A61H 2205/088; A61H 2230/00; A61H 2230/08; A61H 2230/60; A61H 2230/605;
(Continued)

(56) References Cited

U.S. PATENT DOCUMENTS 2,694,395 A    11/1954    Brown
6,719,701 B2    4/2004    Lade
(Continued)

FOREIGN PATENT DOCUMENTS

FR    2939643 B1    12/2012
WO    2016003790 A1    1/2016

OTHER PUBLICATIONS

Hu et al., "Stress Memory Polymers," Journal of Polymer Science Part B: Polymer Physics 53.13 (2015): pp. 893-898.
(Continued)

*Primary Examiner* — Colin W Stuart
(74) *Attorney, Agent, or Firm* — Cantor Colburn LLP; Kristofer Haggerty

(57) ABSTRACT

Embodiments include systems, methods, and products for prevention and treatment of orthostatic hypotension, edema, and nocturia. Aspects include a tubular compression sleeve having an adjustable effective radius. Aspects also include a position sensor. Aspects also include an actuator in communication with the position sensor, wherein the actuator is capable of modifying the effective radius of the tubular compression sleeve.

18 Claims, 7 Drawing Sheets

(51) Int. Cl.
*A61F 5/34* (2006.01)
*A61B 5/11* (2006.01)
(52) U.S. Cl.
CPC .......... *A61H 9/005* (2013.01); *A61H 9/0021* (2013.01); *A61H 9/0071* (2013.01); *A61H 9/0078* (2013.01); *A61H 9/0092* (2013.01); *A61B 5/1116* (2013.01); *A61H 2201/5007* (2013.01); *A61H 2201/5064* (2013.01); *A61H 2230/62* (2013.01); *A61H 2230/625* (2013.01)
(58) Field of Classification Search
CPC .......... A61H 2230/62; A61H 2230/625; A61H 2201/0157; A61H 2201/1628; A61H 2201/1635; A61H 2201/164; A61H 2201/165; A61H 2201/5007; A61H 2201/5025; A61H 2201/5035; A61H 2201/5015; A61H 2201/5053; A61H 2201/5056; A61H 2201/5058; A61H 2201/5061; A61H 2201/5064; A61H 2201/5069; A61H 2201/5071; A61H 2201/5084; A61B 5/022; A61B 5/02233; A61B 5/02; A61F 5/30; A61F 5/32; A61F 5/34
See application file for complete search history.

(56) References Cited

U.S. PATENT DOCUMENTS

| | | | |
|---|---|---|---|
| 8,444,569 B2 | 5/2013 | Laufer | |
| 8,517,963 B2 | 8/2013 | Larson et al. | |
| 9,050,211 B2 | 6/2015 | Siniaguine et al. | |
| 2009/0234262 A1* | 9/2009 | Reid, Jr. | G16H 40/67 601/152 |
| 2011/0066093 A1* | 3/2011 | Vess | A63B 21/0054 601/148 |
| 2012/0065561 A1* | 3/2012 | Ballas | A61H 9/0078 601/152 |
| 2013/0310719 A1* | 11/2013 | Davis | A61H 9/0085 601/149 |
| 2014/0094726 A1 | 4/2014 | Malhi et al. | |
| 2014/0236058 A1* | 8/2014 | Lee | A61H 11/00 601/84 |
| 2014/0336551 A1* | 11/2014 | Mantese | A61H 9/005 601/134 |
| 2014/0358193 A1 | 12/2014 | Lyons et al. | |
| 2015/0038888 A1 | 2/2015 | Allen et al. | |
| 2015/0313608 A1 | 11/2015 | Baudenbacher et al. | |
| 2016/0008204 A1* | 1/2016 | Elliot | A61B 17/135 601/152 |
| 2016/0008206 A1 | 1/2016 | Devanaboyina | |
| 2017/0202724 A1* | 7/2017 | De Rossi | A61B 5/6811 |
| 2017/0312165 A1* | 11/2017 | Johnson | A61H 1/006 |

OTHER PUBLICATIONS

Partsch et al., "Compression for Leg Wounds," British Journal of Dermatology 173.2 (2015), pp. 359-369.
Amos Cahan et al., "Active Adaptable Compression Structures", Related Application, U.S. Appl. No. 15/337,523, filed Oct. 28, 2016.
List of IBM Patents or Patent Applications Treated as Related; (Appendix P), Filed Dec. 12, 2017; pp. 1-2.

* cited by examiner

ACTIVE ADAPTABLE COMPRESSION STRUCTURES

DOMESTIC PRIORITY

This application is a divisional of U.S. application Ser. No. 15/337,523, titled "ACTIVE ADAPTABLE COMPRESSION STRUCTURES", filed Oct. 28, 2016, the contents of which are hereby incorporated by reference in its entirety.

BACKGROUND

The present invention relates generally to active adaptable compression structures, and more specifically to methods, systems, and products including active adaptable compression structures for applying variable compression to a body part for treatment or prevention of cardiovascular disorders, such as orthostatic hypotension, edema, or nocturia.

Orthostatic hypotension is a medical condition in which a person's blood pressure falls upon transition to an upright position, such as when a person transitions from lying down to sitting or standing or from sitting to standing. The decrease in blood pressure can be accompanied by other adverse symptoms, such as dizziness, light-headedness, palpitations, falling, or loss of consciousness. In extreme cases, this loss in blood pressure can result in stroke or angina. Moreover, up to 20% of individuals aged 65 or older experience orthostatic hypotension to some degree. In this population, orthostatic hypotension involves an increased level of complications from falls, for example due to an increased risk for fractures because of reduced bone mass and an increased risk of bleeding because of capillary fragility, increased use of anti-aggregation agents and anti-coagulants.

SUMMARY

In accordance with one or more embodiments of the present invention, a system for applying compression to a body part includes a tubular compression sleeve having an adjustable effective radius. The system also includes a position sensor. The system also includes an actuator in communication with the position sensor, wherein the actuator is configured to modify the effective radius of the tubular compression sleeve.

In accordance with another embodiment of the present invention, a method for treating or preventing orthostatic hypotension includes positioning a tubular compression sleeve on a body part of a patient. The method also includes applying a position sensor to the patient. The method also includes detecting a positional change in the patient with the position sensor. The method also includes, based at least in part upon the detected positional change, modifying an effective radius of the tubular compression sleeve to alter a compression on the body part.

In accordance with a further embodiment of the present invention, a computer program product for treatment of orthostatic hypotension includes a computer readable storage medium readable by a processing circuit and storing program instructions for execution by the processing circuit for performing a method. The method includes receiving, by a processor, a first real-time position for a patient. The method also includes receiving, by the processor, a second real-time position for the patient. The method also includes calculating, by the processor, a difference in position for the patient based upon the first real-time position and the second real-time position. The method also includes determining, by the processor, whether the difference in position for the patient indicates a change in body position. The method also includes, based upon a determination that the difference in position for the patient indicates a change in body position between an upright and an inclined position, signaling an actuator to modify an effective radius of a tubular compression sleeve.

BRIEF DESCRIPTION OF THE DRAWINGS

The subject matter of embodiments of the invention is particularly pointed out and distinctly claimed in the claims at the conclusion of the specification. The foregoing and other features and advantages of the one or more embodiments described herein are apparent from the following detailed description taken in conjunction with the accompanying drawings in which:

FIGS. 4A-4B illustrate operation of an active compression stocking according to one or more embodiments of the invention, in which:

FIG. 4A illustrates a released active compression stocking; and

FIG. 4B illustrates a retracted active compression stocking.

DETAILED DESCRIPTION

Figure 1:
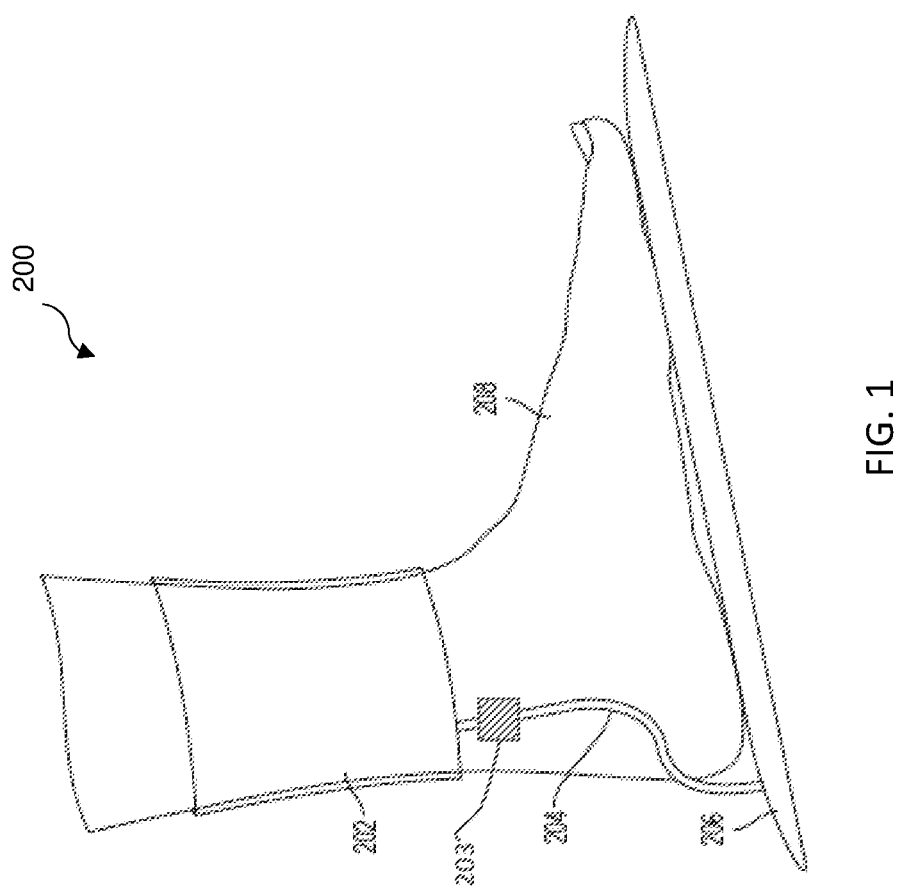
FIG. 1 illustrates an active compression system according to one or more embodiments of the invention.

Embodiments provide methods, systems, and products for treating and preventing orthostatic hypotension or limb edema including active adaptable stockings. In some embodiments, active adaptable stockings apply variable compression to areas of the lower body in response to a change in body position in order to maintain blood pressure at or above a desired threshold level.

Orthostatic hypotension (OH) can be the result of several pathophysiologic processes. As a person transitions from a lying down or sitting position to a standing position, gravitation can pull blood in the venous system towards the lower part of the body. When the venous blood return to the heart is reduced, cardiac output decreases and blood pressure can drop.

Healthy individuals, upon a body position change, can employ a variety of compensatory mechanisms to maintain blood pressure or prevent a rapid decrease in blood pressure. For example, vasoconstriction in the lower limbs can increase blood pressure. Additionally, a heart rate can rise in response to a positional change in order to increase cardiac output, thereby preventing a rapid decline of blood pressure.

In some cases, compensatory reactions are impaired, increasing the incidence of OH. If the autonomic innervation of the heart or arteries is damaged, for example, compensatory reactions are not carried out effectively. Autonomic dysfunction could be a result of a disease affecting sympathetic or parasympathetic branches, such as a neurodegenerative disease or peripheral neuropathy. Intravascular volume depletion can also contribute to OH, and low effective blood volume can be seen in various conditions including dehydration, overzealous diuresis, uncontrolled diabetes, congestive heart failure, and hypoalbuminemia, to mention some. Moreover, various medications, including anti-adrenergic drugs, which are used for hypertension and heart failure, can cause orthostatic hypotension as an adverse reaction. Orthostatic hypotension can also be seen in elderly populations with no recognizable underlying disease. Orthostatic hypotension can co-occur with supine hypertension, complicating treatment for both of these conditions.

OH treatment can include pharmacologic and non-pharmacologic interventions. Treatment can alleviate OH symptoms. Many patients with OH conventionally are forced to tolerate supine hypertension because treatment of supine hypertension can aggravate OH. Supine hypertension is associated with adverse cardiovascular outcomes. Control of supine hypertension can be limited in patients with OH by a drop in blood pressure that accompanies a rise to an upright position. Alleviation of OH symptoms can alleviate treatment limitations on such patients and can, thereby, lead to better control of supine hypertension. Factors such as early time of day, eating, ambient or body temperature change, physical activity, or altered salt or fluid intake can change the severity of OH. For this reason, both pharmacological management and non-pharmacologic interventions can be used.

Limb edema can be caused by a variety of medical conditions, including venous insufficiency and lymphangiectasia. Venous insufficiency is a condition characterized by failure of the venous system to efficiently carry blood back to the heart. Impaired venous return can result from a variety of factors and conditions, such as vein compression, increased intra-abdominal pressure (e.g., during pregnancy), and increased right atrial pressure as a result of cardiomyopathy, valvular heart disease, and other forms of pericarditis. Impaired venous return can be associated with potentially serious complications, including damage to unidirectional valves such that the valves have an impaired ability to prevent blood from flowing backwards from gravitational force. Venous stasis can cause impaired lymphatic drainage of body parts, including the limbs. This can result in edema and deposition of blood products in the skin, leading to hyperpigmentation. Lymphangiectasia can result, for example, from lymph gland lesions, lymphatic vessel abnormalities, and parasitic infection within lymphatic vessels.

In most conditions leading to edema, fluid can accumulate in dependent areas owing to gravitation. Assuming an upright position can aggravate forces leading to edema. Thus, fluid retention in dependent body parts can be maximal during daytime hours. During sleep, however, fluid redistribution can lead to increased venous return and, thereby, increased renal perfusion and increased urine production. Nocturia can cause fragmented sleep and, moreover, is a risk factor for falls.

Turning now to an overview of aspects of the present invention, systems and methods include active adaptable compression structures that treat or prevent a medical condition. In some embodiments, active adaptable compression structures are used to treat or prevent orthostatic hypertension (OH), limb edema or nocturia.

In some embodiments, patients are treated for OH with tight body (or compression) stockings. Compression stockings can reduce the capacitance of the venous bed, thereby preventing a rapid decrease in blood pressure.

In some embodiments, systems and methods include active adaptable compression structure that are easy to apply, cause minimal discomfort, and can prevent or reduce blood pressure decreases in the upright position. In some embodiments, compression is automatically adjusted in response to a patient's change in position. In some embodiments, compression is increased upon a patient rising from a sitting or lying position to counteract the gravitational pull of blood toward lower extremities. In some embodiments, compression is decreased upon a patient's transition from a standing position to a sitting or lying position, or from a sitting to a lying position. In some embodiments, systems and methods apply differential external pressure to limit gravitational pull of biological fluids to lower portions of the body during changes in position of the body.

FIG. 1 illustrates an active compression system 200 according to one or more embodiments of the invention. The system 200 includes a tubular compression sleeve 202. The tubular compression sleeve 202 can have an adjustable effective radius, wherein the effective radius represents the internal radius of the sleeve that comes in proximity to the body. The tubular compression sleeve 202 can be positioned on a body part. As is shown, the tubular compression sleeve can be positioned around a lower limb of a user 208. In some embodiments, the active compression system 200 includes a position sensor. As is shown, a position sensor can include a pressure activated foot pad 206. The foot pad 206 can be connected to the compression sleeve 202 via a connecting pipe 204. In some embodiments, system 200 includes a position sensitive actuator. In operation, the footpad 206 can contain a gas or a liquid. When pressure is applied to the footpad 206, such as when the user assumes an upright position, gas or liquid within the footpad 206 can be forced through the connecting pipe 204 to a fillable internal cavity within the tubular compression sleeve 202. Upon filling the tubular compression sleeve 202, the walls of the tubular compression sleeve 202 can expand, thereby reducing the effective radius and increasing hydrostatic pressure within the lower limb of the user 208. Optionally, in some embodiments, the active compression system can include a valve 203. In some embodiments, the valve 203 can control the degree or rate of inflation or deflation of the compression sleeve 202. Valve 203 can, for example, be a check valve with a variable leak, such that the tubular compression sleeve 202 can remain inflated for a period of time upon removal of pressure from the footpad 206 by a reduced flow rate through the valve 203. In some embodiments, valve 203 prevents over-inflation of the tubular compression sleeve 202, potentially reducing a risk of patient injury due to excessive pressure. In some embodiments, valve 203 is a computer-actuated valve. A computer-controlled valve can be controlled by a computer on the device or remotely by an external computer.

In some embodiments, the active compression system 200 can maintain a therapeutic or preventative compression level as a user walks with the system 200. In some embodiments the system 200 includes a valve to control flow from the tubular compression sleeve 200 to the footpad 206, for example by reducing or stopping flow to the footpad 206 and an inlet check valve on the foot pad 206 or on a pump.

In some embodiments, not shown, a compression sleeve can be connected to a connecting pipe to another type of pressure sensitive pad. For example, in place of a footpad, a gas or liquid filled pressure sensitive pad can be applied to a chair or bed. In operation, the pressure sensitive pad can displace the fluid or gas in response to sitting or lying down.

In some embodiments, the system 200 regulates the pressure applied by a compression sleeve 202. In some embodiments, the system includes a valve to regulate flow from a pressure sensitive pad to a tubular compression sleeve 202. For example, a valve can regulate flow from a footpad 206 through a connecting pipe 204 to a tubular compression sleeve 202. A valve can be, for example, a uni-directional valve, a variable rate bleed valve, an adjustable release valve, or a computer-controlled valve. In some embodiments, pressure applied by a user's body can force the liquid or gas within the pressure sensitive pad, such as a footpad 206, through one or more uni-directional valves into a separate sealed compartment capable of holding a pressurized gas or liquid. In some embodiments, pressure applied by a user's body can force the liquid or gas within the pressure sensitive pad, such as a footpad 206, through one or more computer-controlled valves into a separate sealed compartment capable of holding a pressurized gas or liquid. Once a user assumes an upright position from an inclined position, the content stored within the sealed compartment can be released through one or more valves into a tubular structure worn around a user's body, reducing the effective radius.

In some embodiments, the tubular compression sleeve and/or the pressure sensitive pad contain a plurality of internal compartments. In some embodiments, one or more valves regulate the pressure within the plurality of internal compartments.

The tubular compression sleeve 202 can have any shape designed to surround and compress a desired body part. For example, tubular compression sleeve 202 can be in the form of a cylinder to surround a limb. A tubular compression sleeve 202 can be in the shape of a sock, stocking, girdle, corset, belt, or any other shape that can support exerting compression or pressure on a user's soft tissues or vasculature. Tubular compression sleeves can be applied to any part of the body in need of compression, including a lower body portion, such as a lower limb, pelvis, or lower abdomen, or an upper body portion, including an upper limb (e.g., in case of lymphatic insufficiency following radical mastectomy).

In some embodiments of the invention, the effective radius of a tubular compression sleeve is reduced through inflation of the wall of the tubular structures with a liquid, gas, gel, or other flowable material. In some embodiments of the invention, the effective radius of a tubular compression sleeve is reduced through application of electric energy to electro-active polymers. Such electro-active polymers are known. For example, a tubular compression sleeve can include an electro-active polymer that has a dimension that varies upon application of electric energy, and the effective radius of the compression sleeve can be modified by energizing an electro-active polymer or sections thereof. In some embodiments of the invention, the effective radius of a tubular compression sleeve is reduced by retracting a portion of the tubular compression sleeve.

Position sensors include any device that provides information from which a user's relative body position can be derived. In some embodiments, position sensors include an accelerometer, gyrometer, altimeter, GPS device, or pressure sensor, or combinations thereof. In some embodiments, position sensors include pressure sensors, for example sensors that can detect a user change in position with respect to a surface, including for instance a change in position with respect to a floor, a chair, a table, or a bed. For example, a chair pad can contain a pressure sensor.

For example, in operation, when a user is seated in a chair, pressure can be sensed through a pressure sensor in the seat pad and no compression is applied with the tubular compression sleeve responsive to the pressure signal. When the user rises to a standing position, the pressure sensor in the seat pad can sense the change in position through the reduction of the pressure in the seat pad. Upon detection of the user change in position from a seated to a standing position, the effective radius of the tubular compression sleeve can be reduced and a system can apply compression to the user body part upon which the compression sleeve is positioned.

Figure 2:
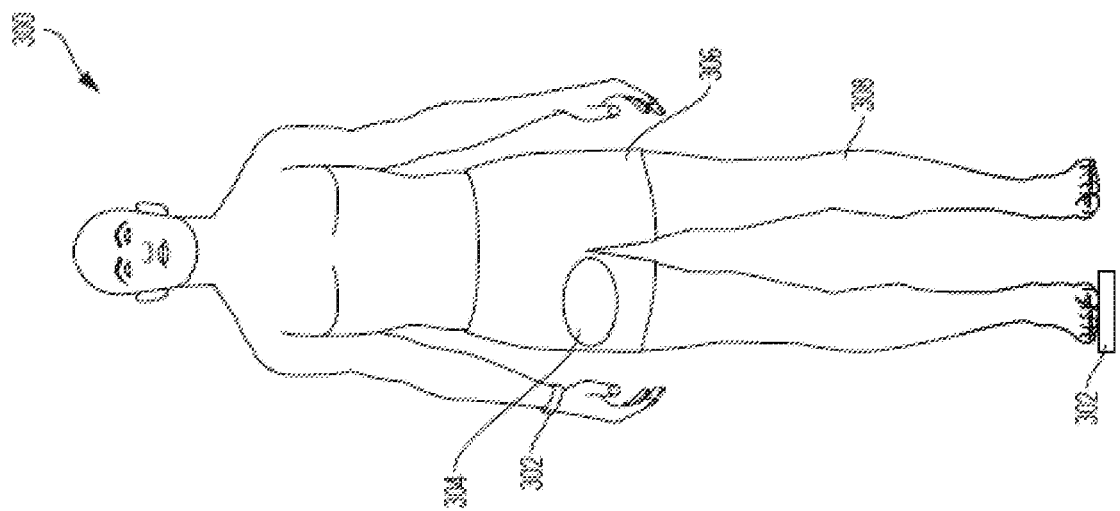
FIG. 2 illustrates a system including a pump-equipped active control stocking according to one or more embodiments of the invention.

FIG. 2 illustrates a system 300 including a pump-equipped active control compression structures according to one or more embodiments of the invention. In some embodiments, a tubular compression sleeve is provided in the form of a pelvic region compression sleeve 306 that is applied to a user 308. As is shown in FIG. 2, the pelvic region compression sleeve 306 can be connected to a pump 304. In some embodiments of the invention, the pump 304 is controlled by input from a position sensor 302. In some embodiments of the invention, the system 300 includes a plurality of positions sensors 302. A position sensor 302 can be included, for example, in a wearable device, such as an accelerometer or gyroscope on a wristband or smartwatch, or in an insole, for example a pressure sensitive insole of a shoe. The position sensor can detect a change in position from an incline or seated position to a more upright position, such as to a standing position. The pump 304 can use gas, liquid (e.g., water or oil), or other flowable materials, such as gel, to increase the pressure within the compression stocking 306. In some embodiments of the invention, the pump 304 is a positive displacement pump, a diaphragm pump, or a piston pump.

Figure 3:
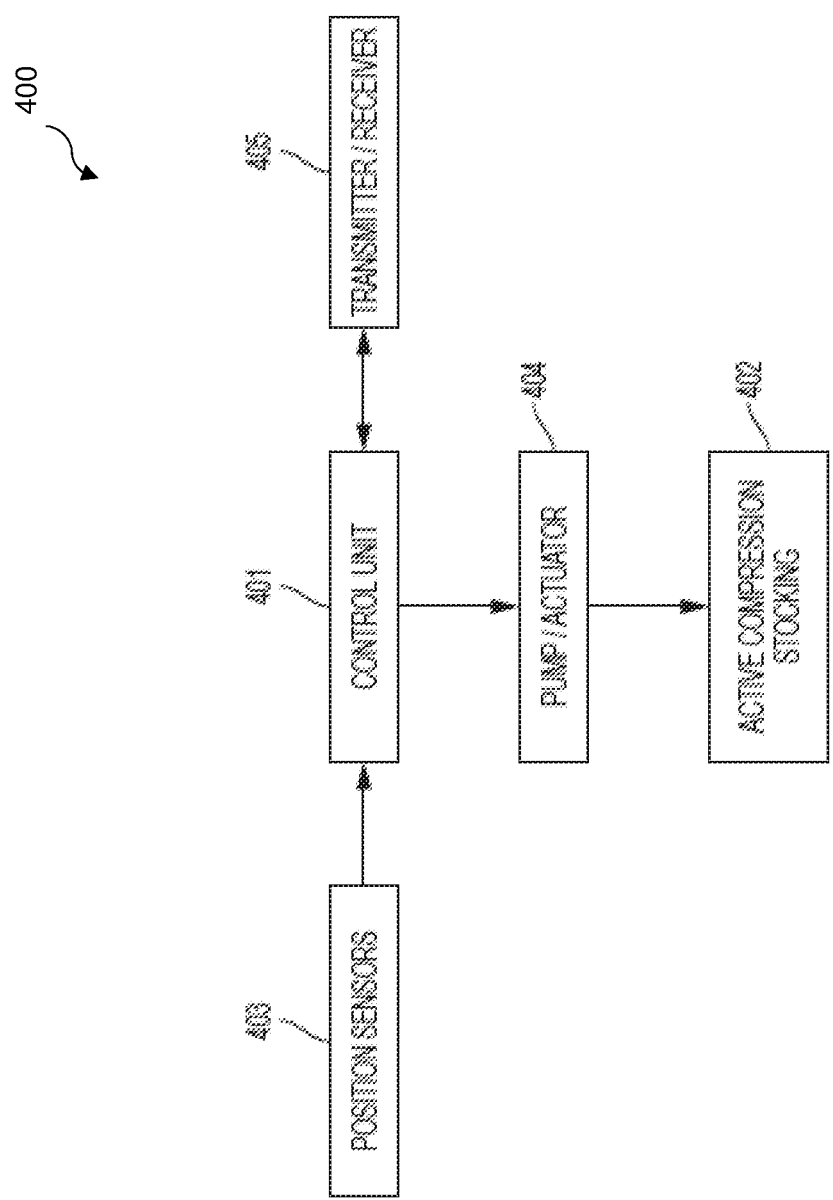
FIG. 3 depicts a schematic of a system for controlling orthostatic hypotension according to one or more embodiments of the invention.

FIG. 3 depicts a schematic of an exemplary system 400 for controlling orthostatic hypotension according to one or more embodiments of the invention. The system 400 includes an active compression structure 402. The system 400 also includes a pump or actuator 404 in communication with the active compression structure 402. In some embodiments, the system 400 includes a control unit 401 that communicates with the pump or actuator 404. One or more position sensors 403 can provide input to the control unit 401. In some embodiments of the invention, the system 400 includes a transmitter and/or receiver 405. A transmitter and receiver 405 can communicate, wirelessly (e.g., WiFi, Bluetooth, RF signal, etc.) or via a wired connection with the control unit 401 to provide input to or from another device. For instance, transmitter and/or receiver 405 can interface with a user through an external device or can connect the system 400 to another control unit or sensor. For example, where the active compression structure 402 is positioned on a first foot, the transmitter and receiver 405 can receive a signal from an external sensor positioned on a second foot to enhance the efficacy of the system for treatment and prevention of OH. The system 400 can optionally include additional sensors, for instance additional position sensors or biosensors, such as heart rate monitors, blood pressure monitors, pulse wave velocity sensors and the like. Input from a biosensor can be analyzed by a control unit 401 along with position sensor 403 input to determine whether to apply compression to a user. In some embodiments, not shown, the system 400 includes a power source.

Figure 4A:
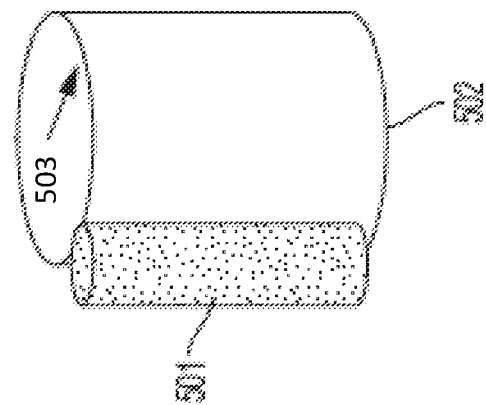
Figure 4B:
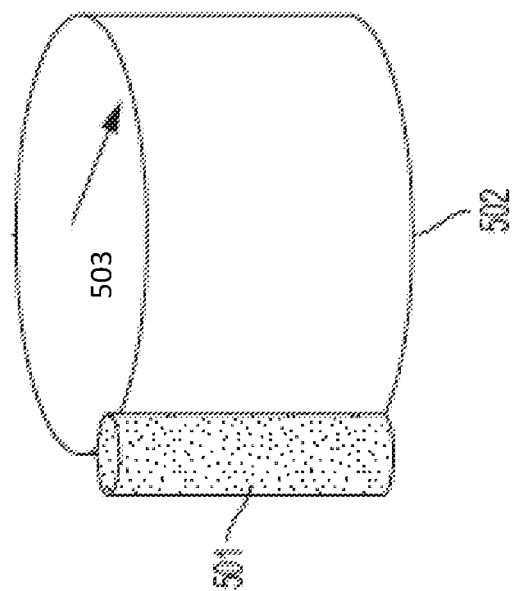

FIGS. 4A-4B illustrate operation of an active compression structure according to one or more embodiments of the invention. FIG. 4A depicts tubular compression sleeve 502 having an effective radius 503. The tubular compression sleeve 502 is connected to a retraction device 501 that is capable of modifying the length of the tubular compression sleeve 502. FIG. 4B illustrates the tubular compression sleeve 502 of FIG. 4A in a retracted position. The retraction device 501 can mechanically reduce the length of the tubular compression sleeve 502, thereby reducing the effective radius 503.

In some embodiments of the invention, compression is applied to a user uniformly through the length of a compression sleeve. In some embodiments of the invention, compression is applied to a user in a gradiated or variable manner through the length of a compression sleeve. Compression can be applied for a period of seconds, minutes or hours. In some embodiments, compression is pulsatile, for instance with a pulsation frequency of 0.001-100 Hertz (Hz).

Figure 5:
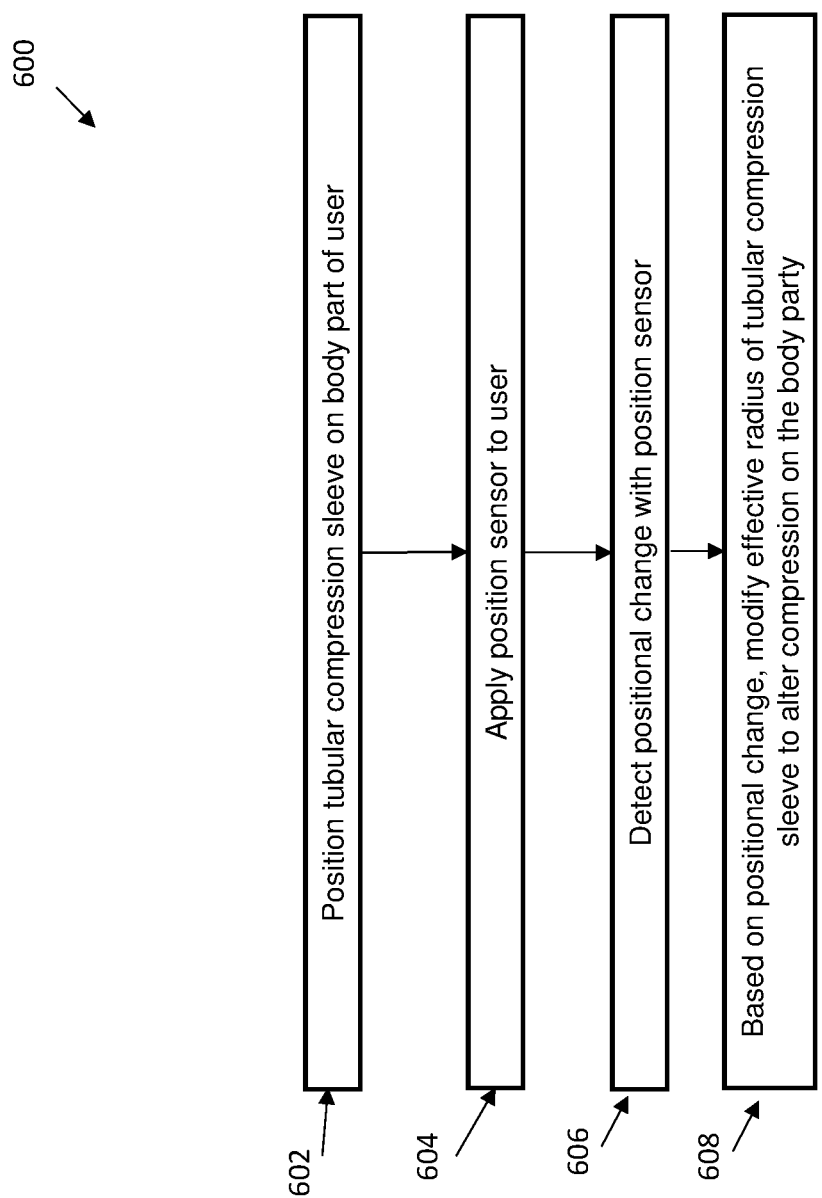
FIG. 5 depicts a flow diagram for a method of treating orthostatic hypotension, edema, or nocturia according to one or more embodiments of the present invention.

FIG. 5 depicts a flow diagram for a method 600 of treating orthostatic hypotension, edema, or nocturia according to one or more embodiments of the present invention. The method 600 includes, as shown at block 602, positioning a tubular compression sleeve on a body part of a user. The method 600 also includes applying a position sensor to a user, as shown at block 604. As shown at block 606, the method 600 includes detecting a positional change with the position sensor. The method 600 also includes, as shown at block 608, modifying an effective radius of the tubular compression sleeve to alter the compression on the body part based upon the positional change.

Figure 6:
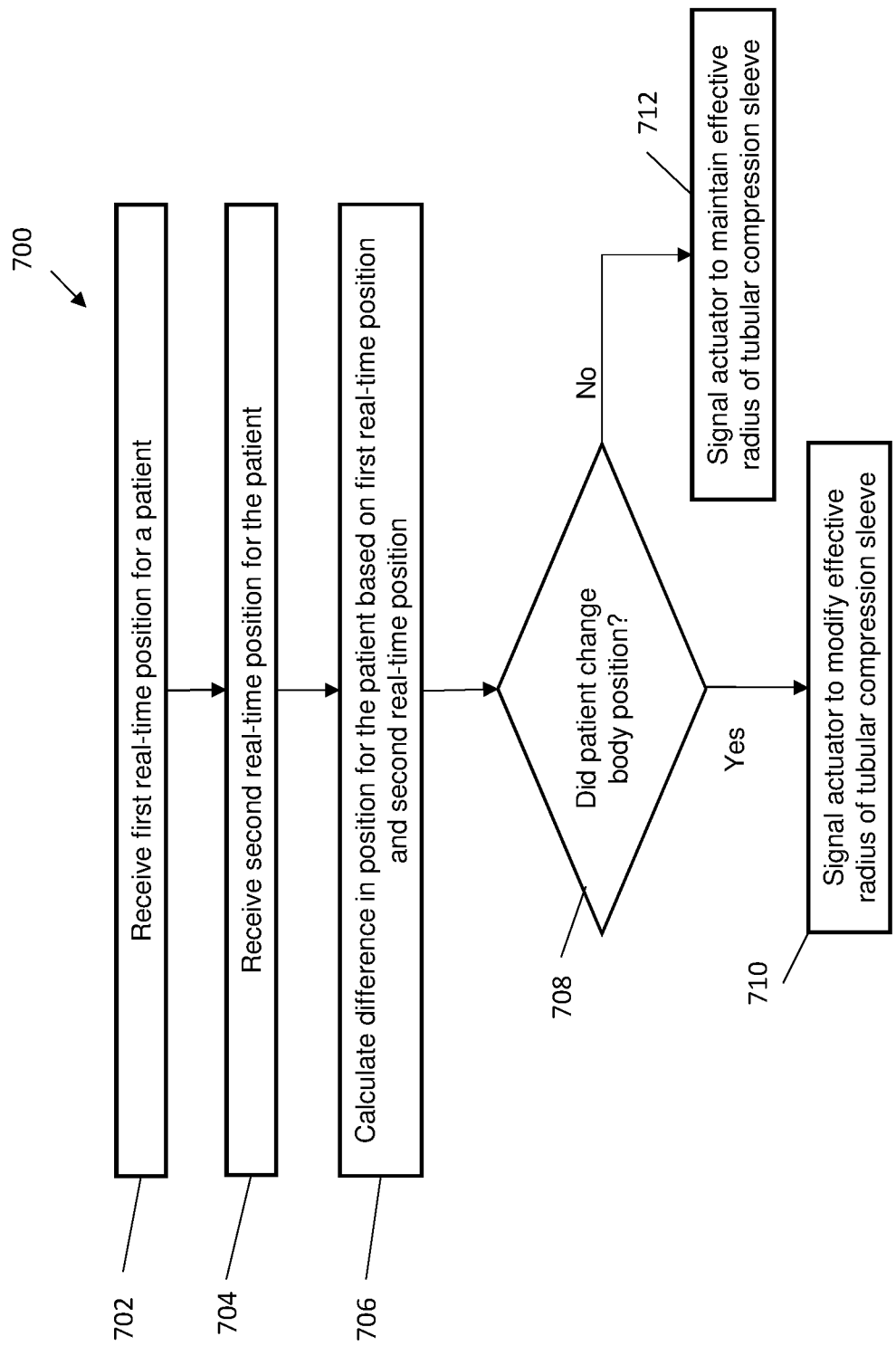
FIG. 6 depicts a flow diagram for another method of treating orthostatic hypotension, edema, or nocturia according to one or more embodiments of the present invention.

FIG. 6 depicts a flow diagram for another method 700 of treating orthostatic hypotension, edema, or nocturia according to one or more embodiments of the present invention. The method 700 includes receiving a first real-time position for a patient, as shown at block 702. The method 700 also includes receiving a second real-time position for a patient, as shown at block 704. The method 700 also includes, as shown at block 706, calculating a difference in position for the patient based upon the first real-time position and the second real-time position. The method 700 then determines whether the patient changes body position, as is shown at decision block 708. Responsive to a determination that the patient changed body position, the method proceeds to block 710 and signals an actuator to modify the effective radius of a tubular compression sleeve. Responsive to a determination that the patient did not change body position, the method proceeds to block 712 and signals an actuator to maintain the effective radius of a tubular compression sleeve.

Figure 7:
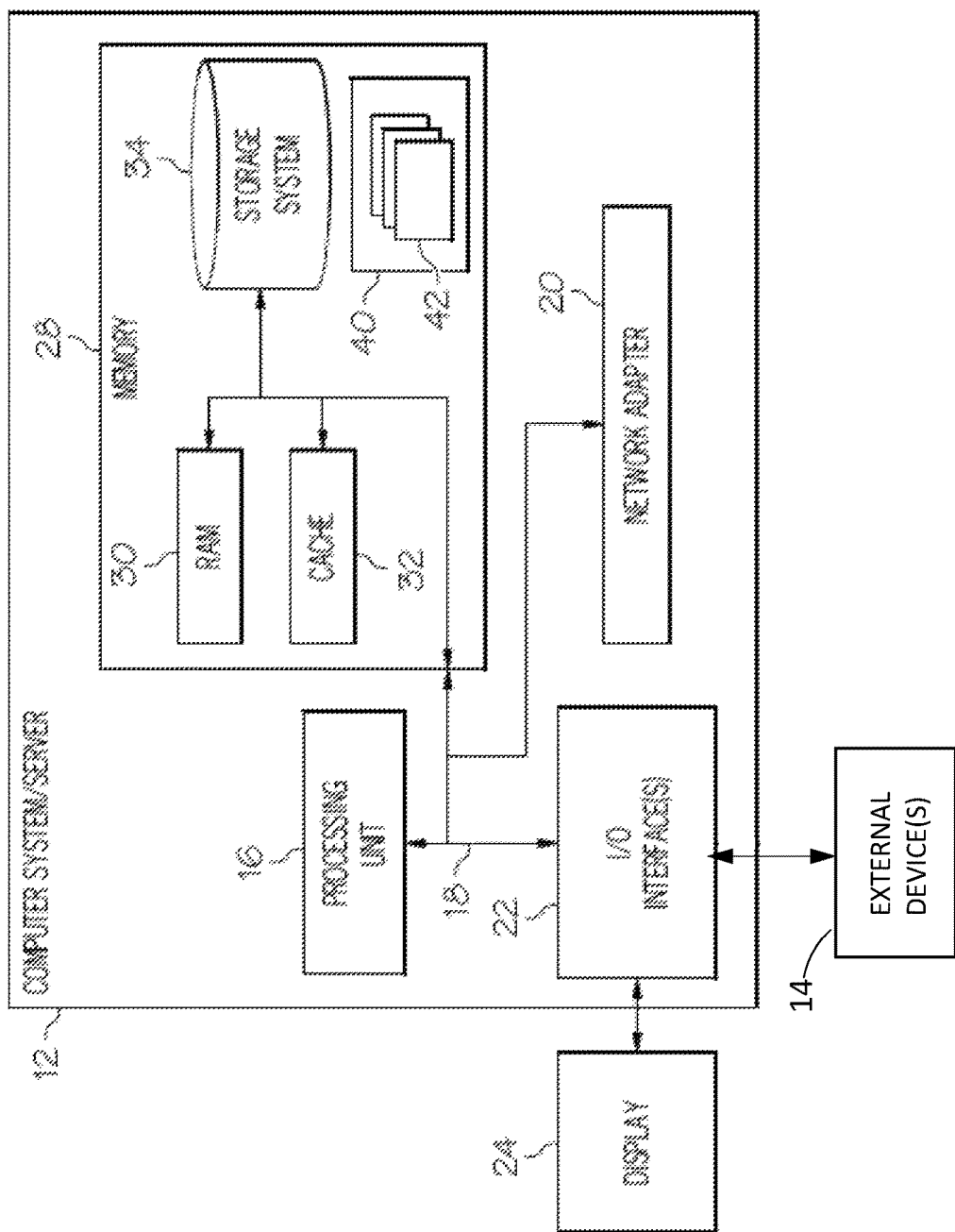
FIG. 7 depicts a computer system according to one or more embodiments of the present invention.

FIG. 7 depicts a computing system node 100 according to one or more embodiments of the present invention. Computer system/server 12 is shown in the form of a general-purpose computing device. The components of computer system/server 12 can include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media can be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 can further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 can include at least one program product having a set (e.g., at least one) of program modules that are configured to carry out the functions of embodiments of the invention.

Program/utility 40, having a set (at least one) of program modules 42, can be stored in memory 28 by way of example, and not limitation, as well as an operating system, one or more application programs, other program modules, and program data. Each of the operating system, one or more application programs, other program modules, and program data or some combination thereof, can include an implementation of a networking environment. Program modules 42 generally carry out the functions and/or methodologies of embodiments of the invention as described herein.

Computer system/server 12 can also communicate with one or more external devices 14 such as a keyboard, a pointing device, a display 24, etc., one or more devices that enable a user to interact with computer system/server 12, and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

The present invention can be a system, a method, and/or a computer program product at any possible technical detail level of integration. The computer program product can include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can include copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein includes an article of manufacture including instructions which implement aspects of the function/act specified in the flowchart and/or block diagram block or blocks.

The computer readable program instructions can also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which includes one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form described. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The flow diagrams depicted herein are just one example. There can be many variations to this diagram or the steps (or operations) described therein without departing from the spirit of embodiments of the invention. For instance, the steps can be performed in a differing order or steps can be added, deleted or modified. All of these variations are considered a part of the claimed invention.

The descriptions of the various embodiments of the present invention have been presented for purposes of illustration, but are not intended to be exhaustive or limited to the embodiments described. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

The invention claimed is:

1. A computer program product for treatment of orthostatic hypotension, the computer program product comprising a non-transitory computer readable storage medium readable by a processing circuit and storing program instructions for execution by the processing circuit for performing operations comprising:
   receiving first real-time position data for a patient from a pressure sensitive insole, the pressure sensitive insole comprising a gas or liquid filled cavity;
   receiving second real-time position data for the patient from the pressure sensitive insole;
   determining that a difference in the position data indicates a change in body position between an upright and an inclined position; and
   signaling an actuator to release the gas or liquid through a variable leak check valve and into a fillable internal cavity of a tubular compression sleeve, thereby modifying an effective radius of the tubular compression sleeve, wherein the variable leak check valve is configured such that the tubular compression sleeve remains inflated for a period of time after removal of pressure from the pressure sensitive insole.

2. The computer program product of claim 1, wherein the operations further comprise determining that the patient has moved to an upright position.

3. The computer program product of claim 2, wherein the operations further comprise signaling an actuator to decrease the effective radius of the tubular compression sleeve.

4. The computer program product of claim 1, wherein the operations further comprise determining that the patient has moved to an inclined position.

5. The computer program product of claim 4, wherein the operations further comprise signaling an actuator to increase the effective radius of the tubular compression sleeve.

6. The computer program product of claim 1, wherein the first real-time position data for a patient comprises a position sensor signal.

7. A processing system for treatment of orthostatic hypotension, comprising a processor in communication with one or more types of memory, the processor configured to perform operations comprising:
   receiving first real-time position data for a patient from a pressure sensitive insole, the pressure sensitive insole comprising a gas or liquid filled cavity;
   receiving second real-time position data for the patient from the pressure sensitive insole;
   determining that a difference in the position data indicates a change in body position between an upright and an inclined position; and
   signaling an actuator to release the gas or liquid through a variable leak check valve and into a fillable internal cavity of a tubular compression sleeve, thereby modifying an effective radius of the tubular compression sleeve, wherein the variable leak check valve is configured such that the tubular compression sleeve remains inflated for a period of time after removal of pressure from the pressure sensitive insole.

8. The processing system of claim 7, wherein the operations further comprise determining that the patient has moved to an upright position.

9. The processing system of claim 8, wherein the operations further comprise signaling an actuator to decrease the effective radius of the tubular compression sleeve.

10. The processing system of claim 7, wherein the operations further comprise determining that the patient has moved to an inclined position.

11. The processing system of claim 10, wherein the operations further comprise signaling an actuator to increase the effective radius of the tubular compression sleeve.

12. The processing system of claim 7, wherein the first real-time position data for a patient comprises a position sensor signal.

13. A computer-implemented method for treatment of orthostatic hypotension comprising
   receiving, by a processor, first real-time position data for a patient from a pressure sensitive insole, the pressure sensitive insole comprising a gas or liquid filled cavity;
   receiving, by the processor, second real-time position data for the patient from the pressure sensitive insole;
   determining, by the processor, that a difference in the position data indicates a change in body position between an upright and an inclined position; and
   signaling, by the processor, an actuator to release the gas or liquid through a variable leak check valve and into a fillable internal cavity of a tubular compression sleeve, thereby modifying an effective radius of the tubular compression sleeve, wherein the variable leak check valve is configured such that the tubular compression sleeve remains inflated for a period of time after removal of pressure from the pressure sensitive insole.

14. The computer-implemented method of claim 13, wherein the method further comprises determining that the patient has moved to an upright position.

15. The computer-implemented method of claim 14, wherein the method further comprises signaling an actuator to decrease the effective radius of the tubular compression sleeve.

16. The computer-implemented method of claim 13, wherein the method further comprises determining that the patient has moved to an inclined position.

17. The computer-implemented method of claim 16, wherein the method further comprises signaling an actuator to increase the effective radius of the tubular compression sleeve.

18. The computer-implemented method of claim 13, wherein the first real-time position data for a patient comprises a position sensor signal.

\* \* \* \* \*